US011865354B1

(12) United States Patent
Sullivan

(10) Patent No.: US 11,865,354 B1
(45) Date of Patent: Jan. 9, 2024

(54) METHODS AND SYSTEMS FOR DISTINGUISHING VT FROM VF

(71) Applicant: West Affum Holdings DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 133 days.

(21) Appl. No.: 16/554,410

(22) Filed: Aug. 28, 2019

Related U.S. Application Data

(60) Continuation-in-part of application No. 16/366,313, filed on Mar. 27, 2019, now Pat. No. 11,471,693, which is a division of application No. 16/268,870, filed on Feb. 6, 2019, now abandoned.

(60) Provisional application No. 62/660,822, filed on Apr. 20, 2018, provisional application No. 62/630,398, filed on Feb. 14, 2018.

(51) Int. Cl.
| | |
|---|---|
| *A61N 1/39* | (2006.01) |
| *A61N 1/04* | (2006.01) |
| *A61B 5/0245* | (2006.01) |
| *A61N 1/02* | (2006.01) |

(52) U.S. Cl.
CPC .......... *A61N 1/3987* (2013.01); *A61B 5/0245* (2013.01); *A61N 1/025* (2013.01); *A61N 1/046* (2013.01); *A61N 1/3904* (2017.08); *A61N 1/3925* (2013.01); *A61N 1/0484* (2013.01)

(58) Field of Classification Search
CPC ..... A61N 1/3987; A61N 1/3925; A61N 1/025
USPC ....................................................... 607/4–8
See application file for complete search history.

(56) References Cited

U.S. PATENT DOCUMENTS

| | | |
|---|---|---|
| 3,724,355 A | 4/1973 | Unger |
| 3,724,455 A | 4/1973 | Unger |
| 4,291,699 A | 9/1981 | Geddes et al. |
| 4,583,524 A | 4/1986 | Hutchins et al. |
| 4,617,938 A | 10/1986 | Shimoni et al. |
| 4,619,265 A | 10/1986 | Morgan et al. |
| 4,895,151 A | 1/1990 | Grevis et al. |

(Continued)

FOREIGN PATENT DOCUMENTS

| | | |
|---|---|---|
| CA | 2942933 A1 | 8/2015 |
| CN | 103405851 A | 11/2013 |
| WO | 98/39061 A2 | 9/1998 |

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.

(Continued)

*Primary Examiner* — John R Downey
(74) *Attorney, Agent, or Firm* — Spectrum IP Law Group LLC

(57) ABSTRACT

Embodiments of a wearable cardioverter defibrillator (WCD) system include a support structure for wearing by an ambulatory patient and at least one processor. When worn, the support structure maintains electrodes on the patient's body, and using the patient's ECG received via the electrodes, the processor determines widths of the QRS complexes, consistency of the QRS complexes, and/or heart rate and uses these determinations to make no-shock, delay-shock, and shock decisions. Shock decisions can be made for heart rates lower than a VF threshold.

25 Claims, 10 Drawing Sheets

(56) References Cited

U.S. PATENT DOCUMENTS

| | | |
|---|---|---|
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,376,104 A | 12/1994 | Sakai et al. |
| 5,381,803 A | 1/1995 | Herleikson et al. |
| 5,394,892 A | 3/1995 | Kenny |
| 5,405,362 A | 4/1995 | Kramer et al. |
| 5,425,749 A | 6/1995 | Adams |
| 5,474,574 A | 12/1995 | Payne et al. |
| 5,554,174 A | 9/1996 | Causey, III |
| 5,601,612 A | 2/1997 | Gliner et al. |
| 5,630,834 A | 5/1997 | Bardy |
| 5,662,690 A | 9/1997 | Cole et al. |
| 5,709,215 A | 1/1998 | Perttu et al. |
| 5,769,872 A | 6/1998 | Lopin et al. |
| 5,782,878 A | 7/1998 | Morgan et al. |
| 5,792,204 A | 8/1998 | Snell |
| 5,803,927 A | 9/1998 | Cameron et al. |
| 5,819,007 A * | 10/1998 | Elghazzawi ............ G16H 50/70 706/46 |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,068,651 A | 5/2000 | Brandell |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,351,671 B1 | 2/2002 | Myklebust et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,694,187 B1 | 2/2004 | Freeman |
| 6,762,917 B1 | 7/2004 | Verbiest et al. |
| 6,941,168 B2 | 9/2005 | Girouard |
| 7,065,401 B2 | 6/2006 | Worden |
| 7,149,576 B1 | 12/2006 | Baura et al. |
| 7,336,994 B2 | 2/2008 | Hettrick et al. |
| 7,379,771 B2 * | 5/2008 | Kovac ............ A61N 1/3621 600/517 |
| 7,460,900 B1 | 12/2008 | Gill et al. |
| 7,559,902 B2 | 7/2009 | Ting et al. |
| 7,865,238 B2 | 1/2011 | Brink |
| 7,870,761 B2 | 1/2011 | Valentine et al. |
| 7,894,894 B2 | 2/2011 | Stadler et al. |
| 7,974,689 B2 | 7/2011 | Volpe et al. |
| 8,024,037 B2 | 9/2011 | Kumar |
| 8,036,746 B2 | 10/2011 | Sanders |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,825,154 B2 | 9/2014 | Jorgenson et al. |
| 8,838,235 B2 | 9/2014 | Cowan et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 8,996,101 B2 | 3/2015 | Zhang et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,533,165 B1 | 1/2017 | Gunderson |
| 9,592,403 B2 | 3/2017 | Sullivan |
| 9,757,579 B2 | 9/2017 | Foshee, Jr. et al. |
| 9,757,581 B2 | 9/2017 | Sullivan et al. |
| 10,016,614 B2 | 7/2018 | Sullivan et al. |
| 10,322,291 B2 | 6/2019 | Medema et al. |
| 11,160,990 B1 | 11/2021 | Sullivan et al. |
| 11,331,508 B1 | 5/2022 | Cowan et al. |
| 2003/0158593 A1 | 8/2003 | Heilman et al. |
| 2003/0187479 A1 * | 10/2003 | Thong ............ A61N 1/39622 607/5 |
| 2004/0049117 A1 | 3/2004 | Ideker et al. |
| 2004/0220623 A1 | 11/2004 | Hess |
| 2004/0230105 A1 | 11/2004 | Geva et al. |
| 2005/0107833 A1 | 5/2005 | Freeman et al. |
| 2005/0107834 A1 | 5/2005 | Freeman et al. |
| 2005/0131476 A1 | 6/2005 | Kim et al. |
| 2006/0017575 A1 | 1/2006 | McAdams |
| 2006/0173364 A1 | 8/2006 | Clancy et al. |
| 2007/0179539 A1 | 8/2007 | DeGroot et al. |
| 2007/0203418 A1 * | 8/2007 | Starc ............ A61B 5/35 600/509 |
| 2008/0208070 A1 | 8/2008 | Snyder et al. |
| 2008/0215103 A1 | 9/2008 | Powers et al. |
| 2008/0306560 A1 | 12/2008 | Macho et al. |
| 2008/0312708 A1 | 12/2008 | Snyder |
| 2008/0312709 A1 | 12/2008 | Volpe et al. |
| 2009/0005827 A1 | 1/2009 | Weintraub et al. |
| 2009/0018595 A1 | 1/2009 | Bharmi et al. |
| 2010/0007413 A1 | 1/2010 | Herleikson |
| 2010/0114248 A1 | 5/2010 | Donofrio et al. |
| 2010/0298899 A1 | 11/2010 | Donnelly et al. |
| 2010/0331904 A1 | 12/2010 | Warren et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0022355 A1 | 1/2012 | Byrd et al. |
| 2012/0059270 A1 | 3/2012 | Grunwald |
| 2012/0108911 A1 | 5/2012 | Drysdale et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0277638 A1 | 11/2012 | Skelton et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2012/0316611 A1 * | 12/2012 | Armoundas ......... A61N 1/3622 607/7 |
| 2013/0085538 A1 | 4/2013 | Volpe et al. |
| 2013/0231711 A1 | 9/2013 | Kaib et al. |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0025132 A1 | 1/2014 | Libbus et al. |
| 2014/0070957 A1 | 3/2014 | Longinotti-Buitoni et al. |
| 2014/0081162 A1 * | 3/2014 | Snell ............ A61B 5/364 600/516 |
| 2014/0150781 A1 | 6/2014 | Capua et al. |
| 2014/0163395 A1 * | 6/2014 | Sapp, Jr. ............ A61B 5/0205 600/483 |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0037636 A1 | 2/2015 | Amsler et al. |
| 2015/0039053 A1 | 2/2015 | Kaib et al. |
| 2015/0105835 A1 | 4/2015 | Thakur et al. |
| 2015/0265845 A1 | 9/2015 | Sullivan et al. |
| 2015/0297107 A1 | 10/2015 | Sullivan et al. |
| 2015/0328472 A1 | 11/2015 | Sullivan et al. |

(56) References Cited

U.S. PATENT DOCUMENTS

| | | |
|---|---|---|
| 2016/0000349 A1 | 1/2016 | Sullivan et al. |
| 2016/0004831 A1 | 1/2016 | Carlson et al. |
| 2016/0007877 A1 | 1/2016 | Felix et al. |
| 2016/0015329 A1 | 1/2016 | Kohlrausch et al. |
| 2016/0067514 A1* | 3/2016 | Sullivan ............... A61B 5/363 607/6 |
| 2016/0074667 A1 | 3/2016 | Sullivan et al. |
| 2016/0082277 A1* | 3/2016 | Foshee, Jr. ............ A61B 5/318 607/5 |
| 2016/0106332 A1* | 4/2016 | Takeshima ............ A61B 5/366 600/509 |
| 2016/0121100 A1 | 5/2016 | Crone et al. |
| 2016/0235320 A1 | 8/2016 | Sarkar et al. |
| 2016/0278698 A1 | 9/2016 | Freeman et al. |
| 2016/0331984 A1* | 11/2016 | Firoozabadi ......... A61N 1/3931 |
| 2016/0353996 A1* | 12/2016 | Fink .................... A61B 5/7235 |
| 2017/0056682 A1 | 3/2017 | Kumar et al. |
| 2017/0157416 A1 | 6/2017 | Medema et al. |
| 2017/0252571 A1 | 9/2017 | Dascoli et al. |
| 2018/0028083 A1 | 2/2018 | Greenhut et al. |
| 2018/0093102 A1 | 4/2018 | Sullivan et al. |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0221648 A1 | 8/2018 | Gustavson et al. |
| 2018/0264279 A1 | 9/2018 | Kim et al. |
| 2018/0318593 A1 | 11/2018 | Sullivan |
| 2019/0030351 A1 | 1/2019 | Sullivan et al. |
| 2019/0030352 A1 | 1/2019 | Sullivan et al. |
| 2020/0164217 A1 | 5/2020 | Sullivan |
| 2022/0032077 A1 | 2/2022 | Sullivan et al. |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

U.S. Appl. No. 62/630,398, filed Feb. 14, 2018, Sullivan.

Corrected Notice of Allowability dated Aug. 9, 2021, to U.S. Appl. No. 16/382,575.

Corrected Notice of Allowability dated Jul. 23, 2021, to U.S. Appl. No. 16/382,575.

Duncker et al. "Real-world Experience of 355 Consecutive Patients with a Wearable Cardioverter/Debrillator—Single Centre Analysis" Europace 2017, No. 19 Supplemental 3, iii304.

EPO Search Report dated Dec. 19, 2018 on EP Application No. 1816221.0-1224.

EPO Search report dated Sep. 27, 2018 on EP Application 18186229.3-1224.

European Search Report of European Application 16202067.1-1666, dated Apr. 25, 2017.

First Office action and Search Report dated Aug. 30, 2018, to CN Patent Application No. 2016111063501.

Non-Final Office action dated Dec. 21, 2020, to U.S. Appl. No. 16/307,990.

Non-Final Office Action dated Mar. 27, 2020, to U.S. Appl. No. 16/038,007.

Olgin JE, Pletcher MJ, Vittinghoff E, et al., "Wearable Cardioverter-Defibrillator after Myocardial Infarction," N Engl J Med Sep. 27, 2018; 379(13):1205-1215.

Schuhmann et al., "Experience with the wearable cardioverter defibrillator (WCD) in high risk cardiac patients from a German single center cohort", Heart Rhythm 2016;13(5):S254.

Second Office Action dated May 18, 2020, to CN Patent Application No. 2016111106350.1.

WCD Performance for Clinical Review, Sullivan et al., "A Novel Wearable Cardioverter Defibrillator With Reduced False Alarm Rate," AHA 2017.

* cited by examiner

SAMPLE COMPONENTS OF WEARABLE CARDIOVERTER DEFIBRILLATOR (WCD) SYSTEM

FIG. 2 SAMPLE COMPONENTS OF EXTERNAL DEFIBRILLATOR

COMPONENTS OF SAMPLE WCD SYSTEM

*MULTIPLE ELECTRODES FOR SENSING ECG SIGNALS ALONG DIFFERENT VECTORS*

*PERTINENT COMPONENTS FOR VT/VF DISCRIMINATION IN AN EXMAPLE EXTERNAL DEFIBRILLATOR*

| Parameter | No Shock | VT | VF |
|---|---|---|---|
| Heart Rate | <150BPM | >150BPM | >200BPM |
| QRS Width | <120mS | >120mS | >120mS |
| QRS Consistency | Don't care | High | Low |

$$totalError(n) = \sum_{m=0}^{length(f)} (f(m) - g(n+m))^{\wedge}2$$

METHODS AND SYSTEMS FOR DISTINGUISHING VT FROM VF

CROSS REFERENCE TO RELATED PATENT APPLICATIONS

This patent application is a Continuation-in-Part of U.S. patent application Ser. No. 16/366,313 filed Mar. 27, 2019, which is a divisional of U.S. patent application Ser. No. 16/268,870 filed Feb. 6, 2019 which in turn claims the benefit of U.S. Provisional Patent Application No. 62/630,398 filed on Feb. 14, 2018. Said application Ser. No. 16/366,313 claims the benefit of U.S. Provisional Patent Application No. 62/660,822, filed on Apr. 20, 2018. Said application Ser. No. 16/366,313, said application Ser. No. 16/268,870, said Application No. 62/630,398, and said Application No. 62/660,822 are incorporated herein by reference in their entireties.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and thus save the patient's life.

All subject matter discussed in this Background section of this document is not necessarily prior art and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present description gives instances of cardiac monitoring systems (e.g., WCD systems), devices, systems, storage media that may store programs, and methods.

In embodiments, a cardiac monitoring system includes a support structure for wearing by an ambulatory patient. When worn, the support structure maintains electrodes on the patient's body. The ECG signal(s) can be analyzed to distinguish between ventricular tachycardia (VT) and VF. In embodiments, the analysis can use heart rate measurements (which can be determined from the ECG signal or signals), widths or durations of the QRS complexes, and consistency of the QRS complexes In a further enhancement, in WCD, external defibrillator (e.g., AED), and ICD embodiments, distinguishing between VT and VF can be used to make a shock/no shock decision. In some embodiments, the analysis can be used to determine whether to quickly shock or delay the shock for depending on whether VF or VT is detected.

DETAILED DESCRIPTION

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
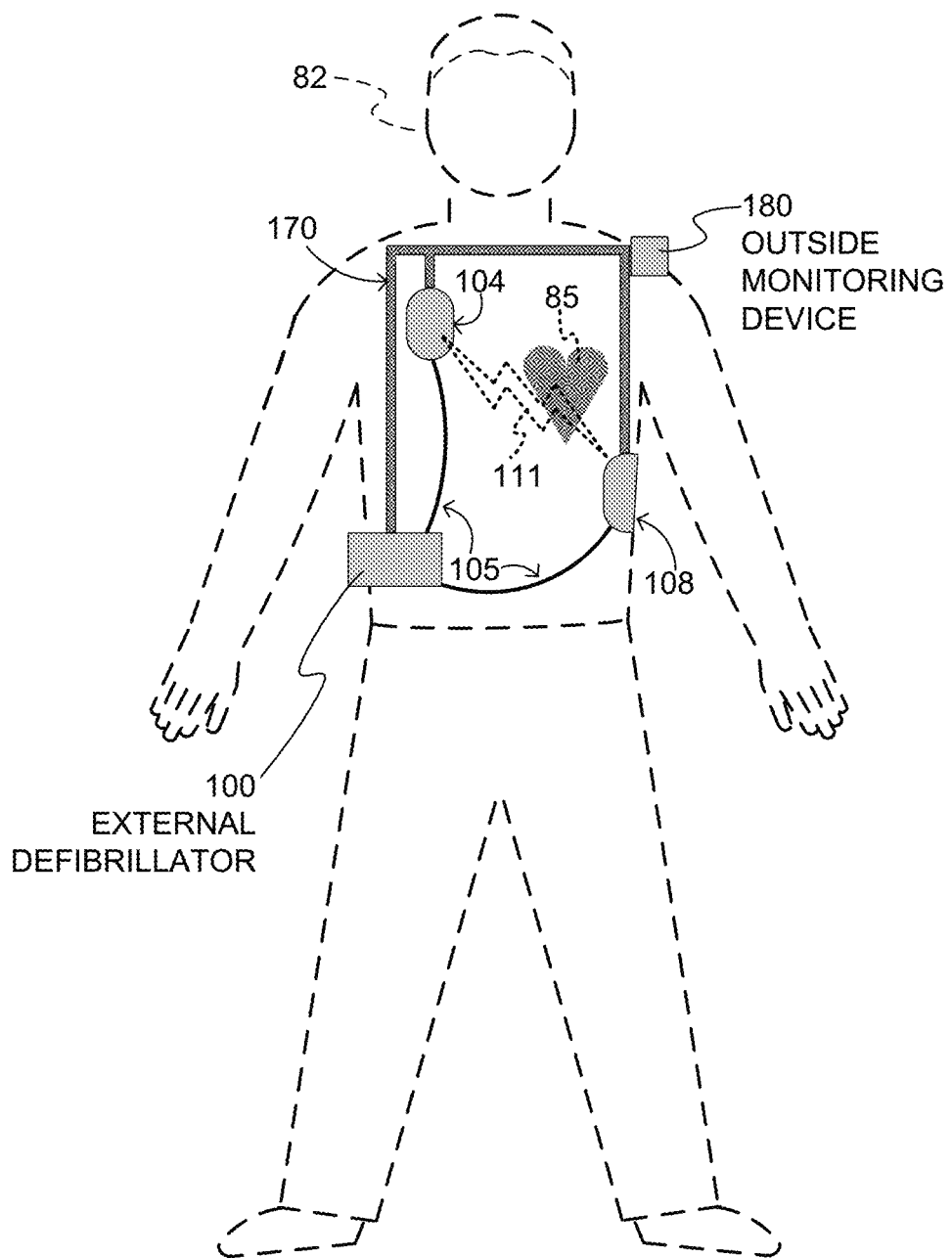
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of U.S. patent application. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein aspor physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
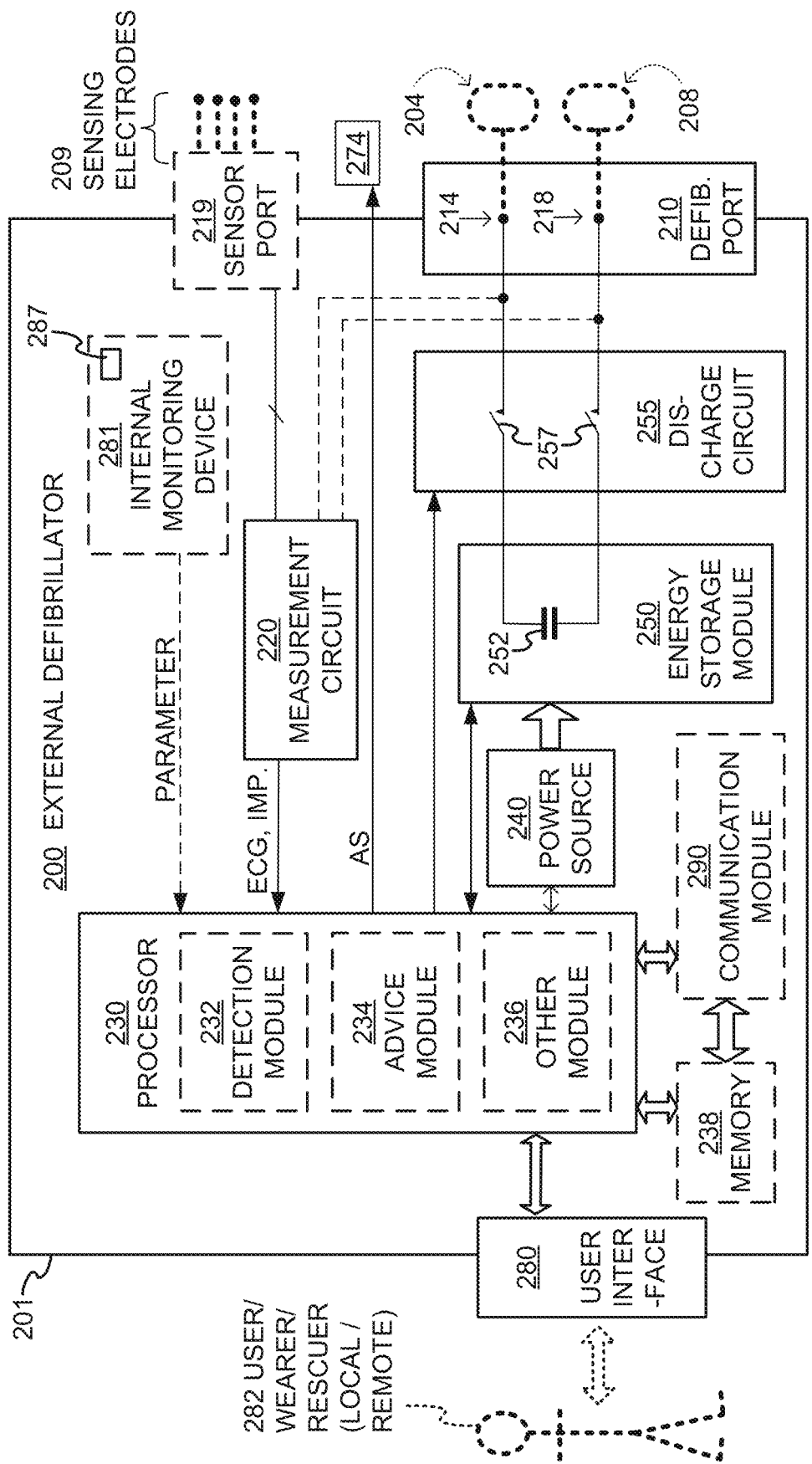
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

Figure 3:
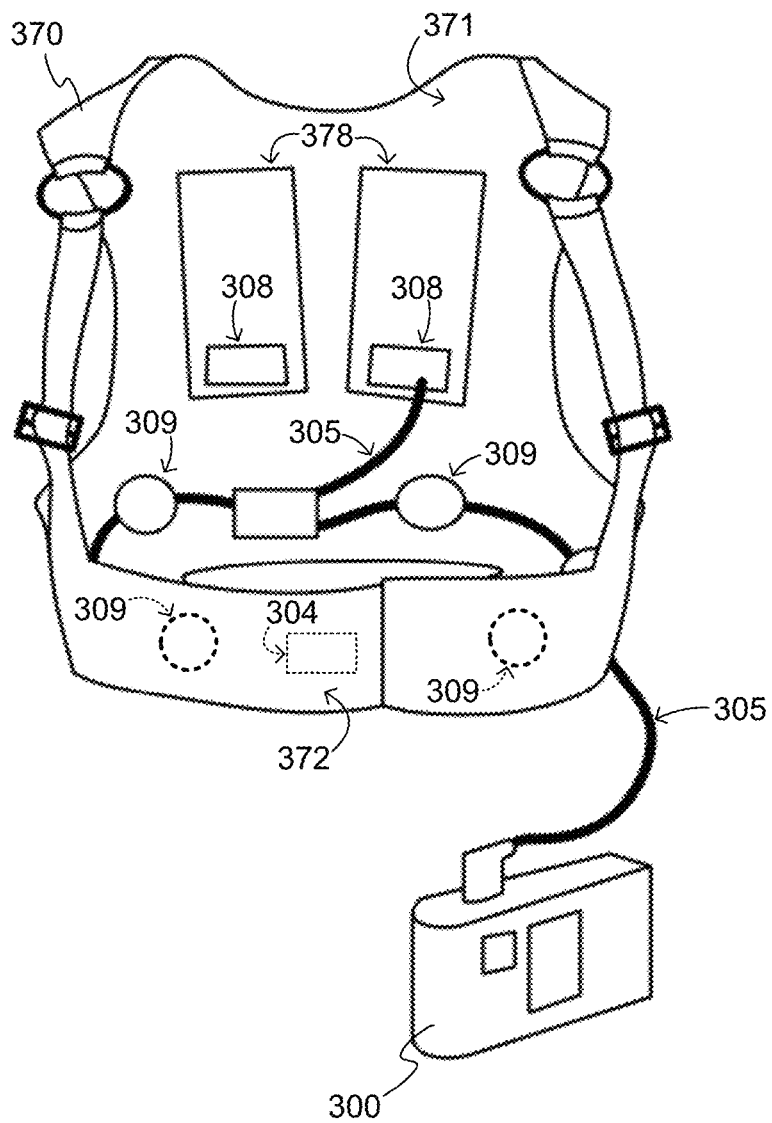
FIG. 3 is a diagram of sample embodiments of components of a WCD system.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
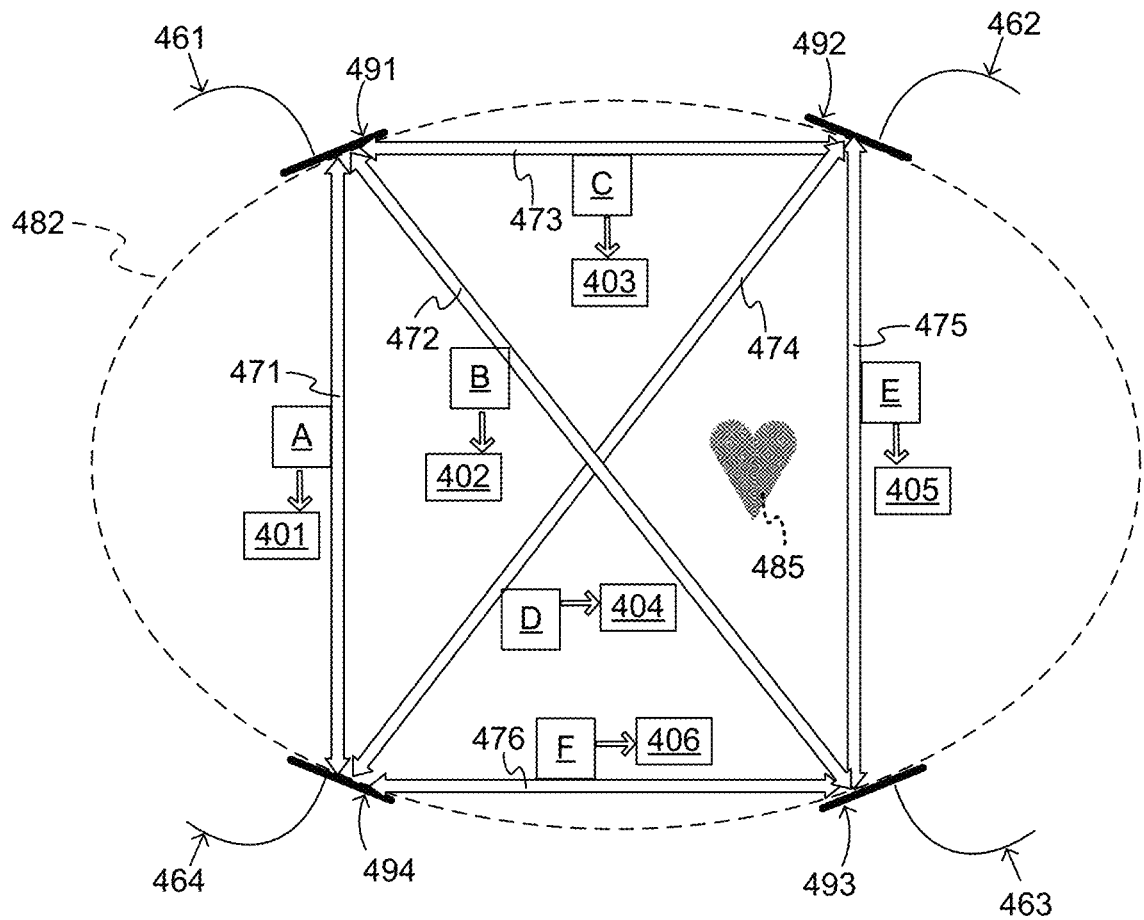
FIG. 4 is a conceptual diagram illustrating how multiple electrodes of a WCD system may be used for sensing ECG signals along different vectors according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either.

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLATOR COMPONENTS MAKING AGGREGATE SHOCK/NO SHOCK DETERMINATION FROM TWO OR MORE ECG SIGNALS", which is incorporated herein by reference.

Figures 5, 6:
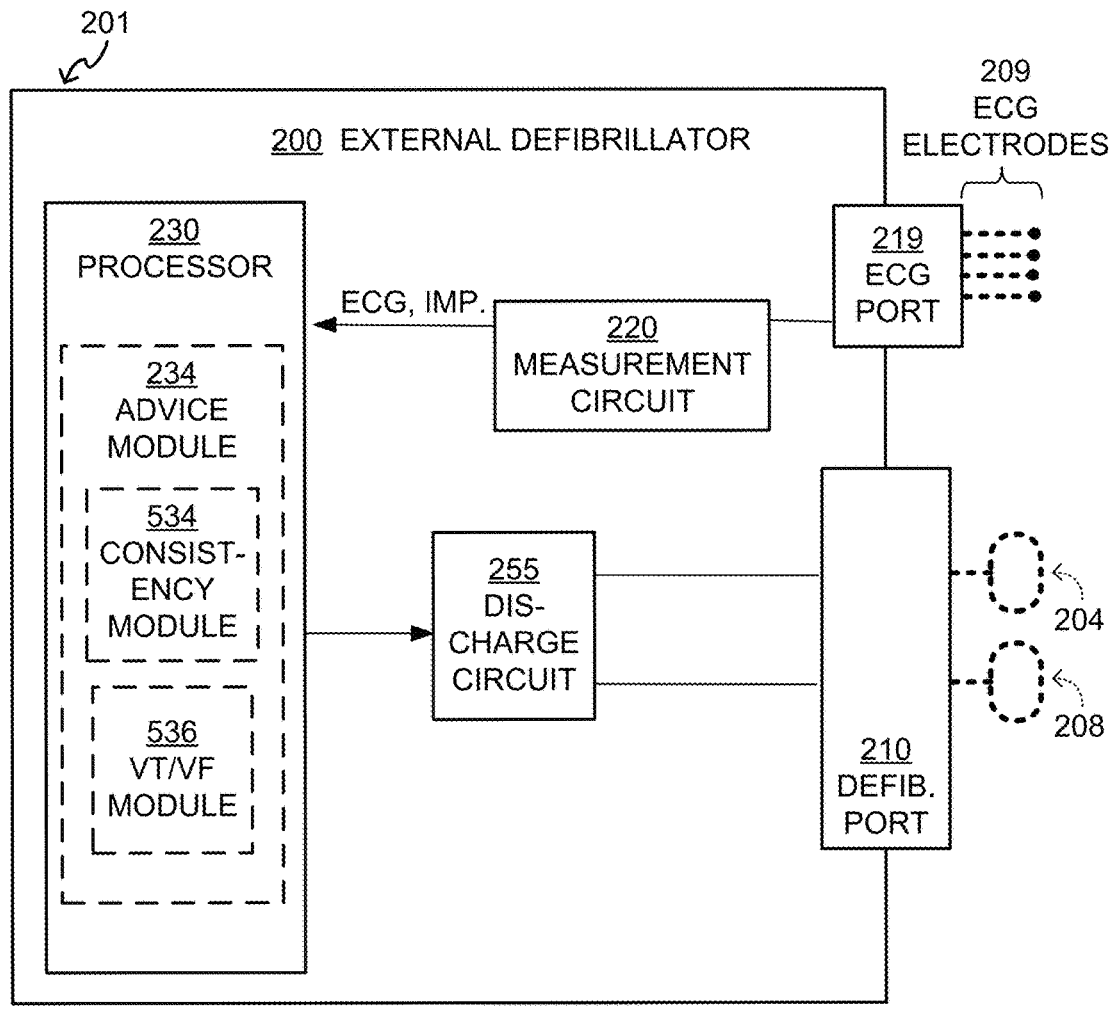
FIG. 5 is a diagram showing some of the components used for VT/VF discrimination in an example external defibrillator, according to embodiments.
FIG. 6 is an example shock decision table, according to embodiments.

FIG. 5 shows pertinent components for distinguishing between VT and VF in an external defibrillator, according to embodiments. For example, the external defibrillator may be a WCD in some embodiments. Other embodiments may be implemented in internal defibrillator such as an ICD.

While external defibrillator 200 in FIG. 5 is based on the diagram of FIG. 2, some of the components not directly used in making a shock/no shock decision are omitted in FIG. 5 for clarity. Those components that are shown in FIG. 5, in embodiments, operate as previously described in conjunction with FIG. 2, with additional functionality provided by a consistency module 534 and a VT/VF module 536. In some embodiments, the VT/VF module 536 is configured to output one or more signals indicative of "shock" or "no shock" outputs based on the heart rate and QRS width determined from the patient's ECG. In some embodiments, consistency module 534 can also be used to determine the consistency of ECG parameters for use in other algorithms, and in some other embodiments modules 534 and 536 can be combined in a single module.

In embodiments, consistency module 534 and VT/VF module 536 are part of advice module 234. In embodiments, advice module 234 can use one or both of consistency module 534 and VT/VF module 536 in making a shock/no shock decision. As will be described below, consistency module 534 and VT/VF module 536 can be advantageously used to discriminate between VT and VF for heart rate—QRS width combinations that can result from either arrhythmia.

Embodiments of advice module 234 can be advantageous over other types of shock/no shock or rhythm analysis approaches in which heart rate is used to assess whether a patient needs to be shocked or not. Heart rate is an imperfect indicator: for example, VF should be shocked, and while it typically presents with a high heart rate (>200 BPM), it sometimes can be much slower. Further, some types of VT should also be shocked. For example, patients experiencing VF and polymorphic VT (PVT) need to be shocked rapidly or they are likely to die. VF typically exhibits a high heart rate, 200 BPM or more. PVT rates vary greatly, but they can occasionally be as slow as 120 BPM. Regardless of the heart rate, these rhythms are non-perfusing and should be shocked quickly.

Monomorphic VT (MVT), on the other hand, may be perfusing or not. In the absence of other information, clinicians typically use the heart rate to assess whether MVT should be shocked. Typically, MVT below 150-170 BPM is tolerated by the patient, while higher rates need to be shocked. MVT also has a tendency to self-terminate. So, while VF and PVT need to be shocked quickly, it may be beneficial to wait and see if MVT self-terminates before delivering a shock. It may be acceptable to wait a minute or two before shocking MVT to allow the MVT to self-terminate and avoid providing an unnecessary shock by a defibrillator.

Supra-ventricular rhythms typically have low heart rates (<100 BPM), but occasionally supraventricular tachycardia (SVT) can have a heart rate higher than 200 BPM. SVT is generally well tolerated by patients, and typically does not need to be shocked by a defibrillator.

After review and analysis of the heart rate ranges indicative of VT, PVT, MVT and/or SVT (which as discussed above can overlap), the inventor of the present disclosure has appreciated that distinguishing between these various heart rhythms independent of the heart rate would be advantageous for both providing shocks when needed and avoiding unnecessary shocks.

Heart Rate/QRS Width Embodiments. In some embodiments, the advice module 234 also uses the QRS width as a separate/additional parameter for making a shock/no shock decision, as shown in FIG. 6. In some embodiments, the advice module 234 is configured to implement the first two rows of table of FIG. 6 so that the QRS width is a parameter used in addition to heart rate.

For example, the VT/VF module 536 of advice module 234 can be configured so that: (1) heart rates below 150 BPM result in a HR output from the VT/VF module 536 that indicates "no shock"; (2) heart rates between 150 BPM-200 BPM are classified as "VT" (which as described above typically do not require a shock except for PVT and some cases of MVT) result in a HR output from the VT/VF module 536 that indicates VT; and (3) heart rates above 200 BPM are classified as "VF" and result in a HR output from the VT/VF module 536 that indicates VF.

In other embodiments, the heart rates defining the "no shock", "VT" and "VF" zones can be different than those described above. For example, the heart rate threshold for "no shock" can be made higher (likely resulting in an increased risk of improper classification of a VT or VF rhythm as "no shock") or made lower (likely resulting in an increased risk of improper classification of a normal rhythm as "VT". This "no shock" threshold can be selected based on the expected accuracy of the HR detection algorithm, the maximum acceptable rate of false "no shock" classifications, the maximum acceptable rate of false "VT" classifications, age and/or health of the patient, etc. as determined empirically from testing on known ECG database(s) and/or from analysis of clinical studies that assess the impact of the different rate thresholds on survival. For particular patients, the rate threshold may be adjusted from the "standard" threshold based on the patient's health and/or age. For example, a young healthy patient may tolerate higher rates and benefit from a higher threshold, while an older or frail patient may benefit from a lower threshold.

Similarly, the heart rate threshold between the "VT" and "VF" classifications can be selected based on the expected accuracy of the HR detection algorithm, the maximum acceptable rate of false "VT" classifications, the maximum acceptable rate of false "VF" classifications, etc.

In addition, in some embodiments VT/VF module 536 is configured so that: (4) a QRS width of less than 120 ms results in a QRS output from VT/VF module 536 that indicates "no shock" (even if the heart rate is between 150 BPM-200 BPM); (5) a QRS width greater than 120 ms is classified "VT/VF" (i.e., can be either VT or VF) and will result in a QRS output from VT/VF module 536 that indicates VT/VF.

In embodiments, the advice module 234 is configured to receive the HR and QRS outputs from the VT/VF module 536 and output a shock/no shock decision. For example, in some embodiments the advice module 234 is configured so that: (1) when the HR output and/or the QRS output indicates "no shock", the advice module 234 is configured to output a "no shock" decision; (2) when the HR output indicates "VF", the advice module 234 is configured to output a "shock" decision; and (3) when the HR output indicates "VT", the advice module 234 is configured to output a "no shock" decision. In some other embodiments, the advice module 234 is configured so that when the HR output indicates "VT", the advice module 234 is configured to output a "delay shock" decision to provide an opportunity for a VT condition to self-terminate. If the VT condition does not self-terminate within a preset or predetermined delay period, the output of the advice module 234 would then change to a "shock" decision. In some embodiments, the "delay shock" decision provides a delay period of 45 seconds to allow the VT condition to self-terminate. In other embodiments, the delay period may range from 5 seconds to 2 minutes.

Figure 7:
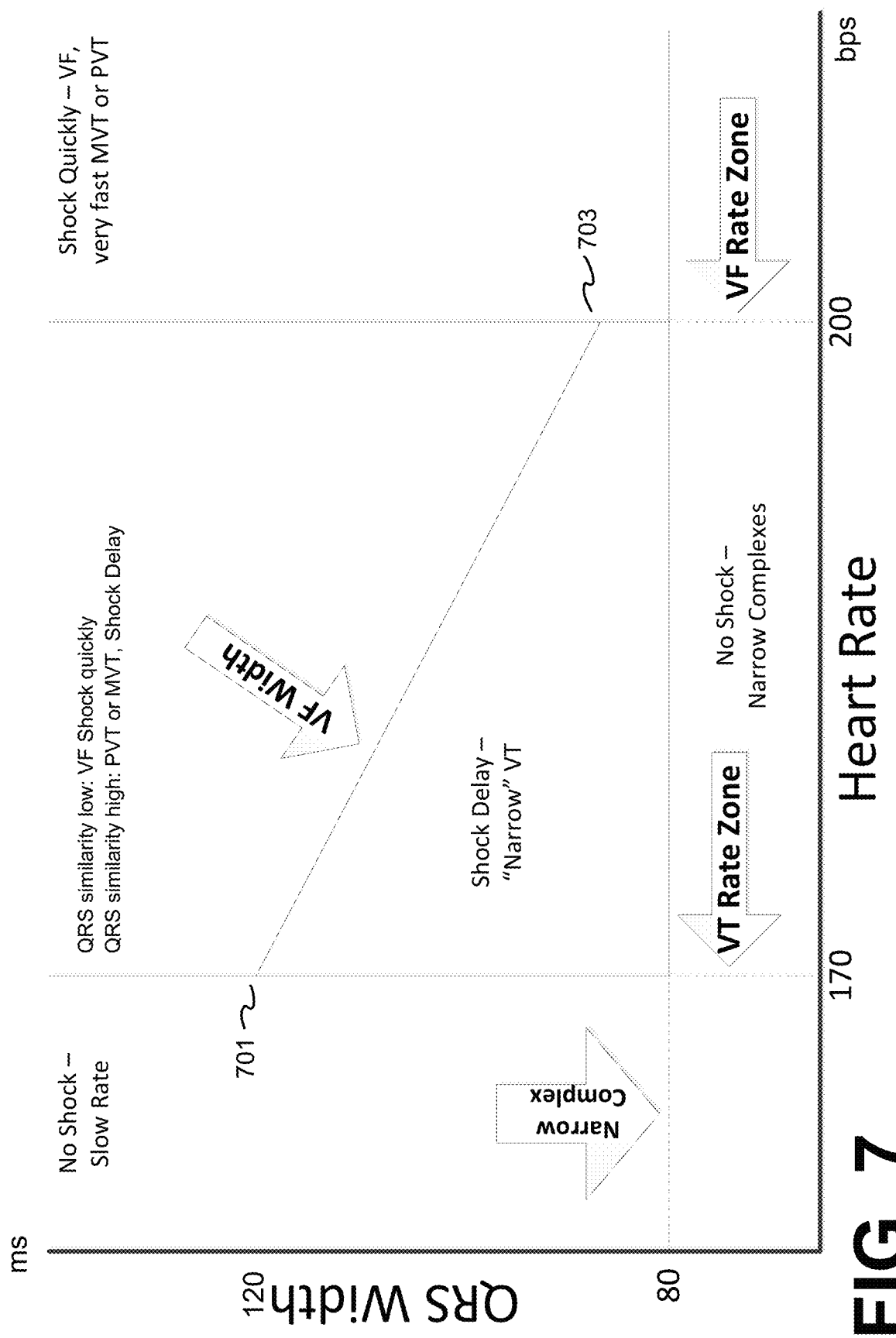
FIG. 7 is a diagram illustrating zones corresponding to VT and VF decisions based on QRS width, heart rate and QRS similarity, according to embodiments.

Some embodiments of advice module 234 and VT/VF module 536 implement a further enhancement referred to herein as "VF Width". In some embodiments, the VF Width is determined as a function of the heart rate and QRS width, bounded by the "no shock" heart rate threshold and the "VF" heart rate threshold. An example VF Width is shown in FIG. 7 for a "VT/VF zone" between 170 BPS and 200 BPS. In this example, the VF Width is a linear function from the point 701 (170 BPS, 120 ms) to the point 703 (200 BPS, 84.6 ms). In other embodiments different functions can be used, including non-linear functions wherein the VF Width in general decreases in QRS width as the heart rate increases within the VT/VF zone.

For ECGs having a heart rate and QRS width that is above the VF Width, advice module 234 is configured to output a "shock" decision in some embodiments. Conversely, in some embodiments for ECGs having a heart rate and QRS width that is below the VF Width, advice module 234 is configured to output a "no shock" decision. In other embodiments, advice module 234 is configured to output a "delay shock" decision (for example, to allow time for a VT rhythm to self-terminate as described above) for ECGs having a heart rate and QRS width that is below the VF Width.

In some embodiments implementing VF Width as in FIG. 7, the VT/VF module 536 is configured to calculate an index according an equation (1):

$$\text{Index} = -39 + (0.14 * \text{Heart Rate}) + (0.13 * \text{QRS Width}). \tag{1}$$

A rhythm with a positive index is classified as "VF" because it might be VF, but a rhythm with wide complexes and a negative index is classified as "VT" because it is unlikely to be VF (based on empirical study of known ECG data).

Heart Rate/QRS Width/QRS Consistency Embodiments. In a further enhancement, some embodiments of advice module 234 also use the output from consistency module 534 as an additional (non-heart rate) parameter for making a shock/no shock decision.

According to some embodiments, consistency module 534 is configured to analyze received QRS complexes and determine whether they are "consistent" or "organized" from beat to beat. As referred to herein, a consistent or organized rhythm is one with a QRS morphology that is similar from beat to beat, while an inconsistent or disorganized rhythm has beat to beat variations in QRS morphology.

A typical QRS complex can be found, or example, by averaging a large number of the previous detected complexes together. In addition, a consistency metric can be determined by comparing a current QRS complex to the calculated typical QRS complex. In some embodiments, the consistency metric may be determined by consistency module 534 at least in part by calculating a value for the similarity between the current QRS complex and the typical QRS complex. Along with the QRS width and heart rate information, the consistency metric can be used by advice module 234 in outputting a shock/no shock decision according to embodiments. For example, a rhythm having heart rate and QRS width above the VR Width in FIG. 7 could be VF, or PVT or MVT as described above in the Heart Rate/QRS Width Embodiments section. The consistency metric from consistency module 534 can be used to distinguish between VF and (PVT or MVT), because VF tends to have low QRS similarity while PVT and MVT tends to have relatively high QRS similarity.

Figures 8, 9:
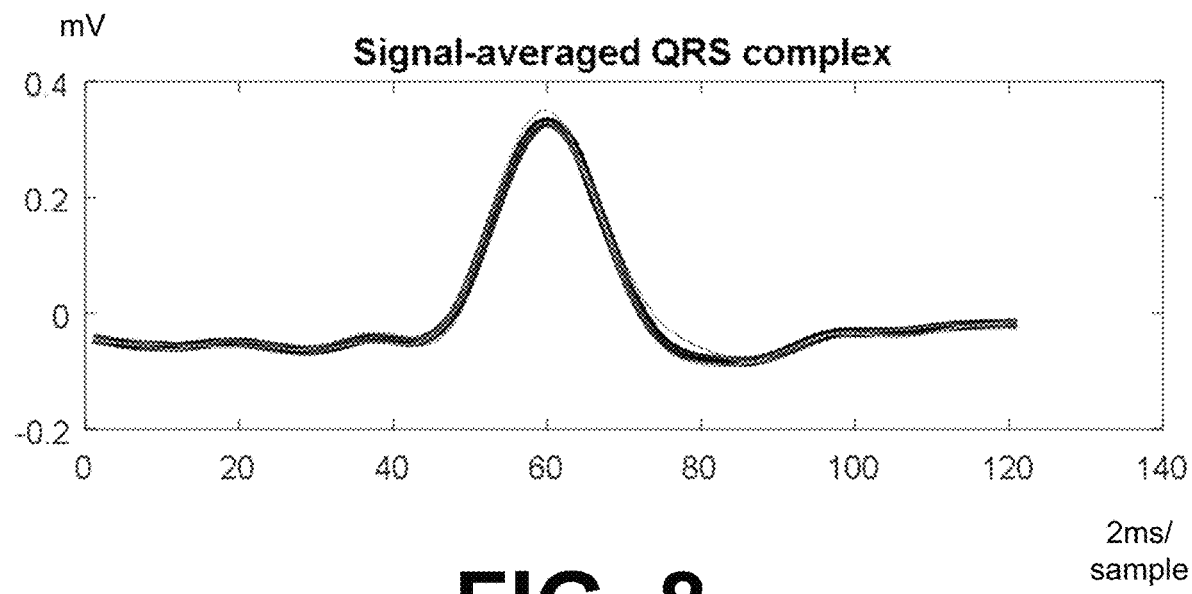
FIG. 8 is a diagram illustrating an example QRS complex similarity.
FIG. 9 shows a sample mathematical equation used in determining QRS similarity, according to an embodiment.

Determining the QRS template: Embodiments. As previously mentioned, the QRS template or "typical QRS complex" can be determined by averaging a number of QRS complexes together, according to embodiments. FIG. 8 shows an example of N QRS complexes from a single channel or vector, measured from a patient having a normal rhythm and plotted together in a time aligned manner. As can be seen in the example of FIG. 8, these QRS complexes from a normal rhythm have a relatively high consistency. In some embodiments, the QRS complexes are taken from a segment (e.g., 4.8 seconds), and these QRS complexes are signal-averaged to determine the QRS template. In some embodiments, two averages are calculated for every segment. In other embodiments, the value of N can be set to a fixed number (e.g., 8) so that the most recent 8 QRS complexes are signal-averaged to determine the template. In yet other embodiments, the N QRS complexes can be the N QRS complexes that were received during the previous number of seconds (e.g., 10 seconds).

The average can be determined in several ways, for example by way on non-limiting examples: applying a least mean squares (LMS) algorithm to the N QRS complexes; applying a recursive least squares filter (RLS); etc. Some embodiments determine the QRS template as described in the previously mentioned (and incorporated herein) U.S. patent application Ser. No. 16/366,313. Other averaging algorithms can be used in other embodiments. In some embodiments the QRS template is determined by the consistency module 554 (FIG. 5).

Determining QRS Consistency: Embodiments. As previously mentioned, some embodiments determine a consistency metric of QRS complexes by calculating the consistency or similarity between a given QRS complex and a typical QRS complex. The consistency or similarity may be determined in a number of ways such as, by way of non-limiting examples: applying a crosscorrelation algorithm to a received QRS complex and a QRS template derived (e.g., averaged) from the previous N QRS complexes, where N is a positive integer); applying an FFT spectral comparison algorithm to the received QRS complex and the QRS template; determining the mean square error or mean absolute error between the received QRS complex and the QRS template (which may require aligning the signals); implementing a match filter derived from the QRS template; etc. For example, some embodiments determine similarity as described below in conjunction with FIGS. 9-10. Other similarity determination algorithms can be used in other embodiments. The determined similarity can then be used to calculate a consistency metric that can be used by the advice module to distinguish VF from VT (e.g., PVT or MVT) for heart rates between the thresholds set for VT and VF (or heart rate/QRS width combinations above the VF width). In some embodiments the consistency is determined by the consistency module 554 (FIG. 5).

Figure 10:
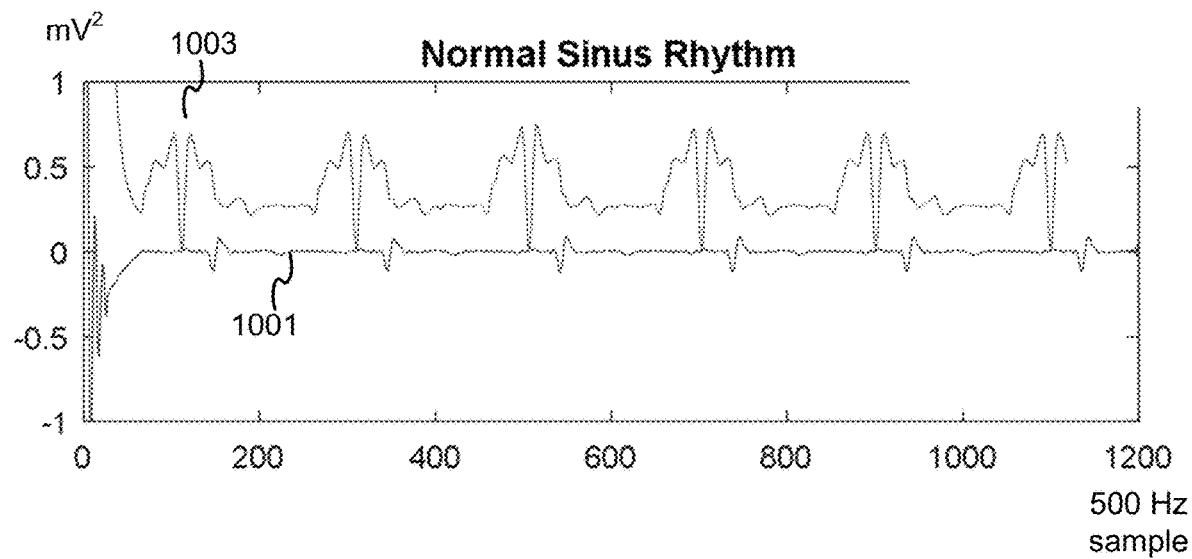
FIG. 10 is a diagram illustrating output of the application of the sample equation of FIG. 9 to a normal sinus rhythm.

FIG. 9 shows a sample mathematical equation used in determining QRS similarity in segment-based ECG monitoring systems, according to an embodiment. In this equation, f(m) corresponds to the QRS template for a segment, and g(n) corresponds to the entire segment. The equation determines a signal totalError in which a value totalError(n) for the nth sample of the received ECG signals during a segment g( ) having a number of samples length(f) by: (a) sliding the typical or template ECG complex f( ) along the entire ECG segment, and (b) for every possible alignment of the samples of the two signals, finding the sum of the squared differences. For a received ECG segment of a normal rhythm, totalError( ) will have a minimum value very close to zero (because in the sliding the QRS template along the segment, the QRS template will at some points be aligned with a QRS complex and since they are very similar in normal rhythms the difference will be close to zero). An example normal ECG signal 1001 and corresponding totalError signal 1003 are shown in FIG. 10. In contrast, a received ECG segment taken during VF will have a minimum value relatively far from zero. Because there is a significant difference in shape of a totalError signal for a normal rhythm compared to a totalError signal for VF, in some embodiments totalError may be used in calculating a consistency metric. One example is described below. In some embodiments the consistency metric is determined by consistency module 554 (FIG. 5).

Figure 11:
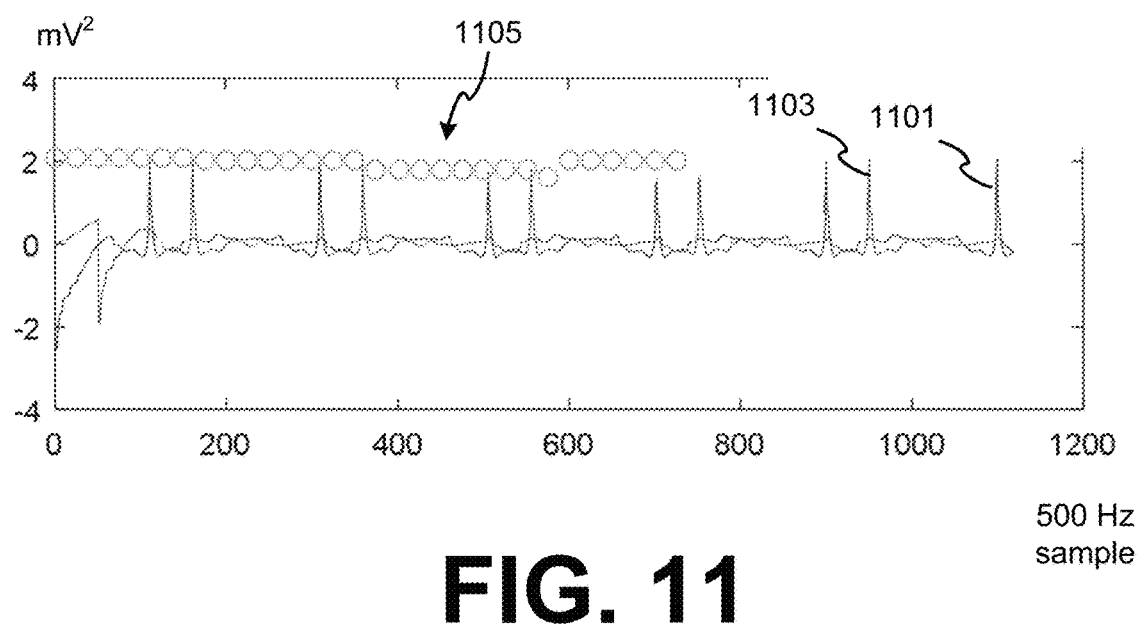
FIG. 11 is a diagram illustrating further processing of the output of the application of the sample equation of FIG. 9 to a normal sinus rhythm.

In some embodiments, the totalError signal is then operated on by a negative log function to "expand" values near zero to help distinguish values that a very close to zero as would be the case for normal rhythms. For example, in some embodiments the –log 10(totalError) is determined to generate a Goodness signal or waveform. Signal 1101 in FIG. 11 is an example of a Goodness signal derived from totalError signal 1003 (FIG. 10). The peaks of the Goodness signal are substantially aligned with the local minimums of the totalError signal, with the amplitude of the Goodness peaks being indicative of how similar the corresponding received QRS complex is to the template QRS complex.

In some embodiments, the consistency metric of a particular QRS complex is calculated as its corresponding Goodness peak. This metric can be calculated segment by segment. In other embodiments, the consistency metric is an average (e.g., a mean) of the Goodness peaks from the most recently received segment or several of the most recently received segments (e.g., 5 segments). In some embodiments, Goodness peaks (or average Goodness peaks) with a value of equal to or greater than 2 are deemed to have a high or good consistency (sometimes referred to herein as being organized or having good organization), while in other embodiments the "threshold" for good consistency can range from 1.5 to 2.5. As described above, high consistency is indicative of VT rather than VF and can be used by the advice module in making a shock/no shock decision.

As a further enhancement, in some embodiments, the Goodness signal or waveform is filtered with a high pass filter to generate a Filtered Goodness signal. In some embodiments, the high pass filter has a cutoff frequency of about 1.5 Hz, but in other embodiments it can range up to 2.5 Hz. Signal 1103 in FIG. 11 is an example of a Filtered Goodness signal derived from Goodness signal 1101. In some embodiments, Filtered Goodness peaks (or average Filtered Goodness peaks) with a value of equal to or greater than 1.98 are deemed to have a high or good consistency, while in other embodiments the "threshold" for good consistency can range from 1.5 to 2.5. As described above, high consistency is indicative of VT compared to VF and can be used by the advice module in making a shock/no shock decision.

In some embodiments, the peaks of the Filtered Goodness signal can be found by finding the maximum value within a window and sliding the window across a preselected number of sample increments. That is, the maximum the biggest value in a certain range (or window) is found, then the window is moved by a bit (e.g., 25 sample increments) and the biggest value is found in this window, and so on. In some embodiments the size of the window is about twice the average spacing between QRS complexes. The number of sample increments that can be obtained in the window depends on the sample rate. For example, in some embodiments the preselected number of sample increments is twenty-five for 250 Hz samples, while in other embodiments the number can range from 1 to 100. This results in an array of peak values referred to herein as Peak Goodness. The points 1105 shown as circles in FIG. 11 illustrate some of the Peak Goodness values. In some embodiments, the consistency metric is determined by taking an average (e.g., the mean) of the Peak Goodness values in the segment (30 in the example of FIG. 11). In other embodiments the number of Peak Goodness values used in calculating the average can depend on size of the segments, which can range for example from 2.5 s to 10 s. In other embodiments, a peak detection algorithm can be run on the Peak Goodness values and then averaged (there would be 5 "peak of peaks" in the example of FIG. 11). In some embodiments, the average Filtered Goodness peaks with a value of equal to or greater than 1.98 are deemed to have a high or good consistency, while in other embodiments the "threshold" for good consistency can range from 1.5 to 2.5. As described above, high consistency is indicative of VT and can be used by the advice module in making a shock/no shock decision.

In an alternative embodiment, the totalError is found only at locations of the QRS detections to simplify the computational burden. Then instead of a Goodness waveform, a single "goodness point" is obtained for each detected QRS complex. The values of the goodness points can then be used to determine a complexity metric similarly to the previously described embodiments (e.g., high pass filtered and averaged), and then compared to a threshold for good consistency.

In some alternative embodiments, the consistency metric is determined using the equation Sum(absolute value(f(m)− g(n+m))) instead of the equation of FIG. 9. In other embodiments, instead of a square term, the equation of FIG. 9 is taken to a different power (e.g., the 4th power).

The above described embodiments can have one or more of the following advantages. The algorithms used to determine the consistency metric are independent of the number of beats in a segment. A positive value of the consistency metric indicates a rhythm that is more organized, which simplifies consistency determinations. The consistency metric algorithms are relatively insensitive to small errors in the location of the detected QRS complexes. The log function used in the consistency metric algorithms can help distinguish differences between the received QRS complex and the QRS template that are very close to zero. The high pass filter in some embodiments tends to give higher organization values to rhythms with tall peaks (like normal QRS complexes) as opposed to sinusoidal shapes (like VF/VT).

The devices and/or systems mentioned in this document perform functions, processes and/or methods. These functions, processes and/or methods may be implemented by one or more devices that include logic circuitry. Such a device can be alternately called a computer, a processor and so on. It may be a standalone device or computer, such as a general-purpose computer, special purpose computer, or part of a device that has one or more additional functions. The logic circuitry may include a processor and non-transitory computer-readable storage media, such as memories, of the type described above in this document. Often, for the sake of convenience, it is preferred to implement and describe a program as various interconnected distinct software modules or features. These, along with data are individually and also collectively known as software. In some instances, software is combined with hardware, in a mix called firmware.

This detailed description includes flow charts, algorithms, and symbolic representations of program operations, which according to some embodiments may be implemented within at least one computer readable medium. Embodiments of flow charts described herein may implement methods, programs, software, firmware, etc.

Figure 12:
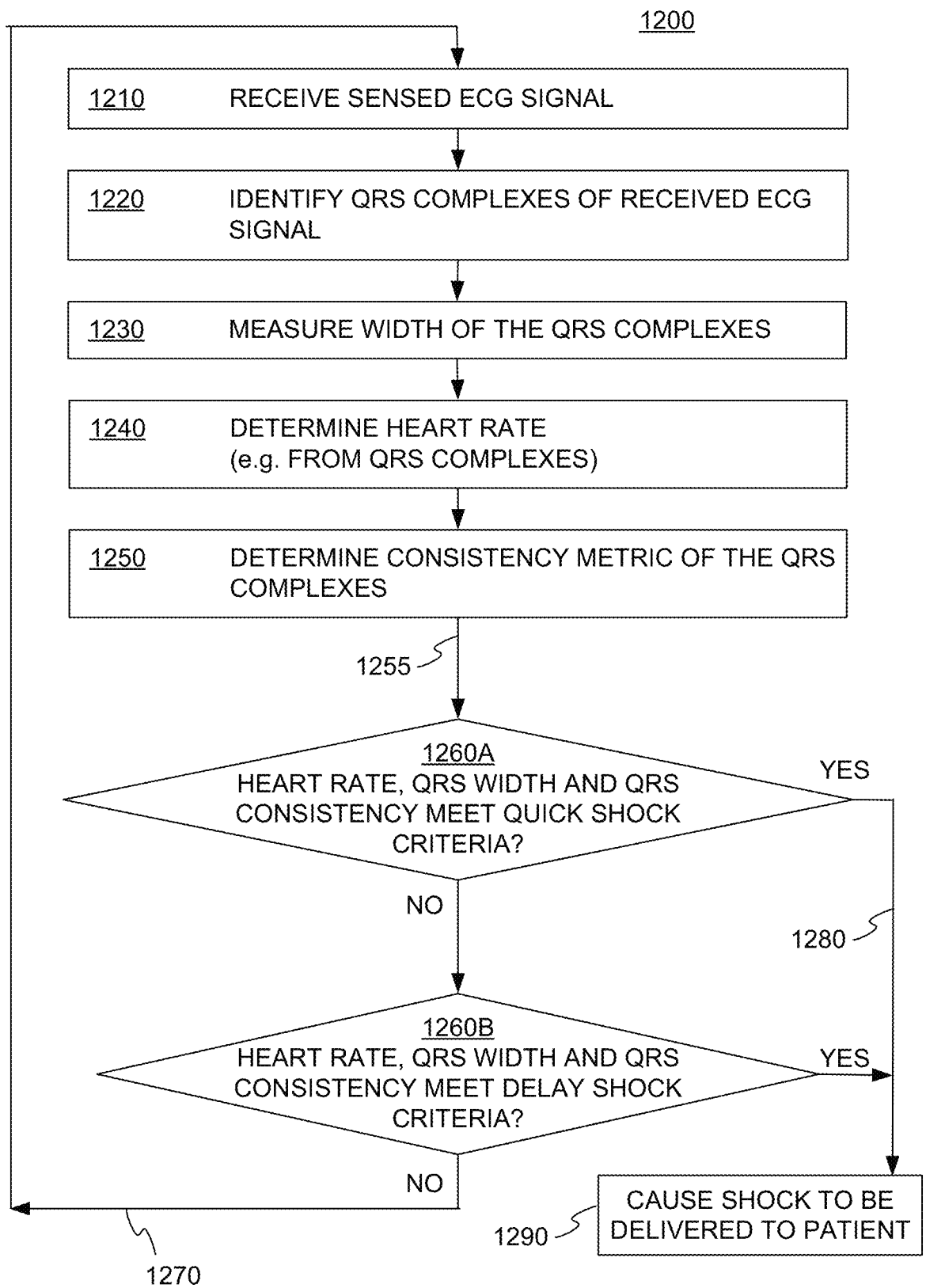
FIG. 12 is a flowchart for illustrating sample methods according to embodiments.

FIG. 12 is a flow chart illustrating embodiments of a method 1200 for FIG. 12 shows a flowchart 1200 for describing methods according to embodiments. In some embodiments, one or portions of method 1200 are implemented using a rules-based system used in the detection and treatment of arrhythmias to improve the performance of a medical device such as, for example, a WCD. As will be recognized, many of the operations of method 1200 can be performed as described above in some embodiments.

Method 1200 may be performed by software, programs, firmware, etc. used by computers, processors, controllers, or devices such as defibrillators (including external and internal defibrillators), heart rate monitors, pacemakers, etc. that incorporate computers, processors, controllers, etc. In some embodiments, method 1200 is performed by WCDs when worn by patients, such as the embodiments of WCDs described above in conjunction with FIGS. 1-5.

According to an operation 1210, the values of the ECG signals may be received. In some embodiments, operation 1210 performed by one or more components of a WCD such as, for example, processor 230 (FIGS. 2 and 5) receiving ECG signals via ECG electrodes 209 and sensor port 219. In other embodiments, a processor remote from the WCD can receive the ECG signals such as, for example, a server or a smartphone-type device communicatively coupled to the WCD. In some embodiments, the WCD uses a segment-based Shock Advisory Algorithm and the portion of the ECG signal is a segment of length 4.8 seconds. In other embodiments, the segment length can range from 2.5 to 15 seconds.

According to another operation 1220, QRS complexes of the ECG signal segments may be identified. Identification may be performed based on the received values. In some embodiments, the QRS complexes are identified or detected by a processor or monitor such as, for example, processor 230 with detection module 232 (FIG. 2.) or by a server or a smartphone-type device communicatively coupled to the WCD. In some embodiments, the QRS complexes are identified or detected as described in U.S. patent app. publication No. 20180264279 entitled "WEARABLE CARDIOVERTER DEFIBRILLATOR (WCD) SYSTEM EVALUATING ITS ECG SIGNALS FOR NOISE ACCORDING TO TALL PEAK COUNTS", filed Feb. 22, 2018. In other embodiments, QRS complexes can be detected using other techniques such as, for example, matched filters, Pan-Tompkins algorithm, etc.

According to another operation 1230, width values of the QRS complexes may be measured. In some embodiments, the widths of the QRS complexes are determined by a processor or monitor such as, for example, processor 230 with detection module 232 (FIG. 2.) or by a server or a smartphone-type device communicatively coupled to the WCD. In some embodiments, the width of the detected QRS complexes is determined as described in U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE", filed Oct. 23, 2018. In other embodiments, widths of the QRS complexes can be determined using other techniques such as, for example, by measuring the peak-trough width and doubling it, the half amplitude width, or the width at the zero crossing, etc.

According to another operation 1240, the patient's heart rate is determined or measured. In some embodiments, the heart rate may be computed from the received QRS complexes by a processor or monitor such as, for example, processor 230 with detection module 232 (FIG. 2.) or by a server or a smartphone-type device communicatively coupled to the WCD. In some embodiments, the heart rate is determined as described in the aforementioned U.S. Pat. No. 10,105,547. In other embodiments, the heart rate may be determined from other heart rate sensors such as an SpO2 sensor, acoustic sensors, pulse plethysmograph, or similar technology used in fitness trackers and smartwatches.

According to another operation 1250, a consistency of the received QRS complexes is determined. In some embodiments, the consistency is characterized as a consistency metric that can be determined by comparing a current QRS complex to a calculated typical QRS complex. In some embodiments, the consistency metric may be determined by consistency module 534 (FIG. 5) at least in part by calculating a value for the similarity between the current QRS complex and the typical QRS complex by a server or a smartphone-type device communicatively coupled to the WCD. In some embodiments, the QRS consistency is the average of Peak Goodness derived from the received QRS complexes as described above in conjunction with FIGS. 5-11.

After operation 1250, method 1200 can proceed as indicated by a process flow line 1255 to an operation 1260A, according to embodiments. According to operation 1260A, the heart rate, the consistency and the QRS width are processed and compared to one or more quick shock criteria. In some embodiments, certain combinations of heart rate, QRS width and consistency are characterized as VT, VF or non-shockable rhythms similar to that in the table of FIG. 6 such that, for example:

(a) a heart rate below a rate threshold (e.g., 150 PBM) would result in a no-shock decision (i.e., would not meet the quick shock criteria);

(b) a QRS width below a width threshold (e.g., 120 ms) would result in a no-shock decision (i.e., would not meet the quick shock criteria);

(c) a heart rate between about 150 BPM and 200 BPM, a QRS width greater than 120 ms and a high consistency would result in a VT decision (i.e., would not meet the quick shock criteria);

(d) a heart rate between about 150 BPM and 200 BPM, a QRS width greater than 120 ms and a low consistency would result in a VF decision (i.e., would meet the quick shock criteria);

(e) a heart rate between greater than 200 BPM would result in a VF decision (i.e., would meet the quick shock criteria); and (f) a QRS width greater than 120 ms and a low consistency would result in a VF decision (i.e., would meet the quick shock criteria).

In other embodiments, different criteria or criterion can be used to make a quick shock decision, including different heart rate thresholds, different QRS width thresholds and/or different consistency metrics.

When, at operation 1260A the answer is NO, then method 1200 can proceed to an operation 1260B, according to embodiments. According to operation 1260B, the heart rate, the consistency and the QRS width are processed and compared to one or more delay shock criteria. In some embodiments, the one or more delay shock criteria include a delay period, and certain combinations of heart rate, QRS width and consistency that are characterized as VT, VF or non-shockable rhythms. In some embodiments, the delay period is 45 seconds, but can range from 5 sec to 2 minutes in other embodiments. In some embodiments, the combinations of heart rate, QRS width and consistency occurring with the delay period are mapped to VT or VF similar to that in the table of FIG. 6. For example:

(g) a heart rate below a rate threshold (e.g., 150 PBM) would result in a no-shock decision (i.e., would not meet the delay shock criteria);

(h) a QRS width below a width threshold (e.g., 120 ms) would result in a no-shock decision (i.e., would not meet the delay shock criteria);

(i) a heart rate between about 150 BPM and 200 BPM, a QRS width greater than 120 ms and a high consistency would result in a VT decision (i.e., in some embodiments would meet the delay shock criteria if sustained for a duration of 45, but would not meet the delay shock criteria if the VT self-terminates before this duration);

(j) a heart rate between about 150 BPM and 200 BPM, a QRS width greater than 120 ms and a low consistency would result in a VF decision (i.e., would not meet the delay shock criteria);

(k) a heart rate between greater than 200 BPM would result in a VF decision (i.e., would not meet the delay shock criteria); and (l) a QRS width greater than 120 ms and a low consistency would result in a VF decision (i.e., would not meet the delay shock criteria).

In other embodiments, different criteria or criterion can be used to make a delay shock decision, including different heart rate thresholds, different QRS width thresholds, different consistency metrics, and/or different durations for criterion (i).

When at operation 1260B the answer is NO (indicating that neither the quick shock nor delay shock criteria were met), method 1200 may return to operation 1210 as indicated by a process flow line 1270. However, when the answer is YES (indicating the delay shock criteria is met)

method 1200 can proceed, as indicated by a process flow line 1280, to an operation 1290. According to embodiments of operation 1290, a shock is delivered to the patients. In some embodiments the WCD delivers a shock to the patient as described above in conjunction with FIG. 2.

Referring back to operation 1260A, when the answer is YES (indicating a quick shock decision is made), method 1200 can also proceed to operation 1290 for delivery of a shock to the patient.

Figure 13:
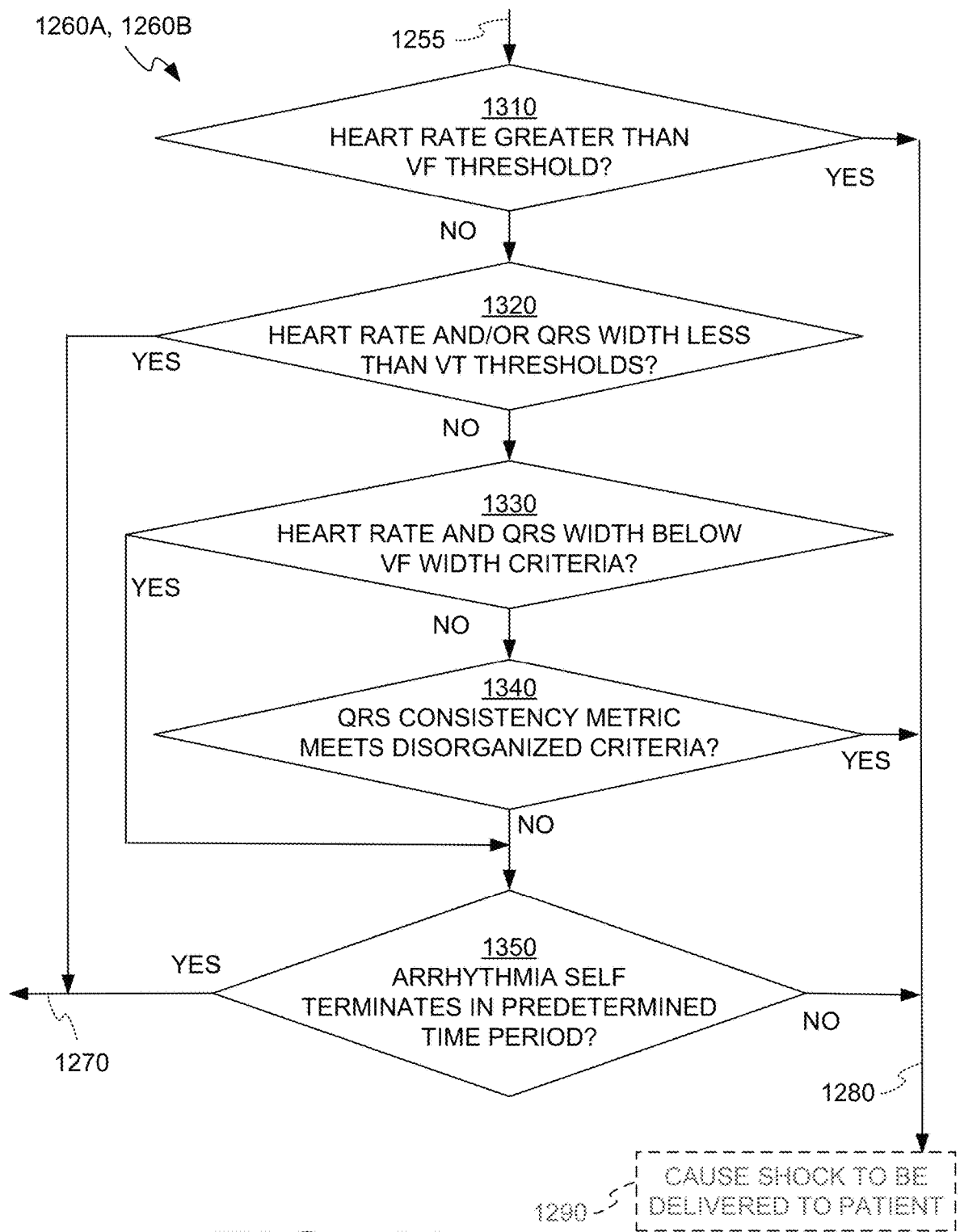
FIG. 13 is a flowchart for illustrating sample methods for implementing some operations depicted in FIG. 12, according to embodiments.

Referring to FIG. 13, in some embodiments, operations 1260A and 1260B are "combined", in effect, so that for each combination of heart rate, QRS width, and consistency is "mapped" to a "no shock" decision, a "delay shock" decision, and a "quick shock" decision rather than performing each of these operations separately. For example, in some embodiments this is implemented as a multi-input look-up table.

According to some embodiments, an operation 1310 is performed after operation 1250 (FIG. 12) as indicated by process flow line 1255. In operation 1310, the patient's heart rate is compared to a VF threshold. In some embodiments, this VF threshold is 200 BPM, but can range from 150 to 250 BPM in other embodiments. If the heart rate is greater that the VF threshold, the operational flow proceeds to operation 1290 (FIG. 12) as shown by process flow line 1280. However, if in operation 1310 the patient's heart rate is less than the VF threshold, the operation flow can proceed to an operation 1320.

According to embodiments of operation 1320, the patient's heart rate is compared to a VT threshold for heart rate, and the patient's QRS width is compared to a VT threshold for QRS width. In some embodiments, the VT threshold for heart rate is 170 BPM but can range from 130 to 200 BPM in other embodiments, and the VT threshold for QRS width is 120 ms but can range from 80 to 160 in other embodiments. When the heart rate and/or the QRS width is less than its corresponding VT threshold, the patient's rhythm is deemed a non-shockable rhythm. The operational flow for a non-shockable rhythm proceeds via process flow line 1270 to operation 1210 (FIG. 12). However, when in operation 1320 the heart rate and QRS width are greater than the corresponding VT thresholds, the operation flow proceeds to an operation 1330.

According to embodiments of operation 1330, the heart rate and QRS width is compared to one or more VF width criteria. In some embodiments, the VF width criteria is defined using equation (1) described above. In such embodiments, when the index calculated according to equation (1) is positive, the heart rate—QRS width combination is above (i.e., not below) the VF width criterion, and the operational flow proceeds to an operation 1340. In some embodiments this reflects that the heart rate—QRS width combination may be VF or VT, which can be analyzed using one or more additional criteria.

Conversely, when the index calculated according to equation (1) is negative, the heart rate—QRS width combination is below the VF criterion and the operational flow proceeds to an operation 1350. In some embodiments this reflects that the heart rate—QRS width combination is likely VT. Some embodiments of the method of FIG. 13 include operations to provide an opportunity for VT to self-terminate.

According to embodiments of operation 1340, a QRS consistency metric is compared to one or more disorganization or disorganized criteria. In some embodiments, the QRS consistency metric is determined as described above in conjunction with FIGS. 8-11. When the QRS consistency metric meets the one or more disorganized criteria the patient's rhythm is reflective of VF, and the operational flow proceeds via process flow line 1280 to operation 1290 (FIG. 12) to cause a shock to be delivered to the patient. However, when the QRS consistency metric does not meet the one or more disorganized criteria the patient's rhythm is reflective of VT, and the operational flow proceeds to operation 1350.

According to embodiments of operation 1350, the patient's rhythm (e.g., heart rate, QRS width and QRS consistency) is monitored for a predetermined time period. As described in operation 1340, the patient's rhythm is likely VT to reach operation 1350. If during the predetermined time period the VT self-terminates (e.g., the heart rate and/or the QRS width decrease below the VT thresholds described above in conjunction with operation 1320), the rhythm is deemed non-shockable and the operational flow proceeds via process flow line 1270 to operation 1210 (FIG. 12). However, if at the end of the predetermined time period the patient's heart rhythm remains in VT, the operational flow proceeds via process flow line 1280 to operation 1290 (FIG. 12).

In some embodiments, operation 1350 is implemented by repeatedly performing operations 1310-1340 until the predetermined time period expires. In such embodiments, operation 1350 may result in performance of operation 1290 (FIG. 12) before the expiration of the predetermined time period if, for example, the patient's heart rate and/or QRS width increases to exceed their corresponding VF thresholds.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein.

The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system capable of being used by an ambulatory patient, the WCD system comprising:
    an energy storage module configured to store an electrical charge;
    a plurality of electrodes;
    a support structure configured to be worn by the patient and structured to position the plurality of electrodes to contact a body of the patient while the support structure is worn by the patient; and
    one or more processors configured to:
        receive at least one ECG signal of the patient via one or more of the plurality of electrodes,
        identify QRS complexes of the received ECG signal,
        determine a consistency metric of the QRS complexes, wherein the consistency metric is determined by:
            evaluating a difference function between a template QRS complex and the identified QRS complexes to determine an error between the template QRS complex and the identified QRS complexes, wherein the difference function comprises a sum of squared differences between the template QRS complex and the identified QRS complexes,
            applying a logarithm function to the error to determine an expanded error,
            calculating the consistency metric from the expanded error, wherein the consistency metric comprises a Goodness signal, and an amplitude of one or more peaks in the Goodness signal are indicative of a similarity between the template QRS complex and the identified QRS complexes, and
            high pass filtering the Goodness signal to provide a filtered Goodness signal for evaluation of the consistency metric;
        determine whether a shock criterion is met based at least in part on the consistency metric; and
        responsive to a determination that a shock criterion is met, cause at least some of the stored electrical charge to be discharged through at least one of the plurality of electrodes to deliver therapy to the patient.

2. The WCD system of claim 1, wherein a heart rate detector is configured to determine the patient's heart rate based at least in part on the received ECG signal.

3. The WCD system of claim 2, in which the one or more processors is configured to implement the heart rate detector.

4. The WCD system of claim 1, in which the one or more processors is further configured, responsive to the consistency metric, to classify the received ECG signal into one of a plurality of rhythm types, the plurality of rhythm types including at a least non-shockable rhythm type, a VF rhythm type, and a VT rhythm type, wherein an ECG signal being classified into the VF rhythm type corresponds to a determination that a shock criterion is met.

5. The WCD system of claim 4, in which the one or more processors is configured to:
   determine whether one or more delay shock criteria is met based on heart rate, width values, and consistency metric, and
   in response to a determination that one or more delay shock criteria is met, to monitor the patient's ECG signal for a predetermined time period after the received ECG signal was classified into the VT rhythm type.

6. The WCD system of claim 5, in which responsive to the patient's ECG signal remaining in the VT classification for the predetermined time period, the one or more processors are configured to determine that a shock criterion is met.

7. The WCD system of claim 5, in which determining whether one or more delay shock criteria is met comprises determining whether an index value, derived from the heart rate and the width values, is greater than a predetermined index threshold or is less than the predetermined index threshold.

8. The WCD system of claim 7, in which determining whether one or more delay shock criteria is met further comprises determining whether a consistency metric is greater than a predetermined disorganized threshold or the consistency metric less than the predetermined disorganized threshold.

9. The WCD system of claim 8, in which responsive to the index value being less than the predetermined index threshold, the one or more processors is configured to determine that one of the one or more delay shock criteria is met.

10. The WCD system of claim 8, in which responsive to the index value being greater than the predetermined index threshold and the consistency metric is less than the predetermined disorganized threshold, the one or more processors is configured to determine that a shock criterion is met.

11. The WCD system of claim 1 further comprising:
   a heart rate detector configured to detect the heart rate of the patient, and
   wherein the one or more processors are further configured to measure width values of the QRS complexes and wherein the determination of whether the shock criterion is met is further based on the heart rate from the heart rate detector and the width values.

12. The WCD system of claim 1, wherein evaluating the difference function comprises finding a sum of differences to a power of 2 or greater between values of the template QRS complex and values of the identified QRS complexes.

13. The WCD system of claim 1, wherein evaluating the difference function comprises finding a sum of absolute values of differences between values of the template QRS complex and values of the identified QRS complexes.

14. The WCD system of claim 1, wherein evaluating the difference function comprises determining a mean square error between values of the template QRS complex and values of the identified QRS complexes.

15. The WCD system of claim 1, wherein evaluating the difference function comprises determining a mean absolute error between values of the template QRS complex and values of the identified QRS complexes.

16. A non-transitory computer-readable storage medium storing one or more programs which, when executed by at least one processor of a wearable cardioverter defibrillator ("WCD") system, the WCD system further including an energy storage module configured to store an electrical charge, a plurality of electrodes, and a support structure configured to be worn by a patient and structured to position the plurality of electrodes to contact a body of the patient while the support structure is worn by the patient, execution these one or more programs causing the WCD to perform operations comprising:
   receiving at least one ECG signal of the patient via one or more of the plurality of electrodes;
   identifying QRS complexes of the received ECG signal;
   measuring width values of the QRS complexes;
      determining a consistency metric of the QRS complexes, wherein the consistency metric is determined by:
         evaluating a difference function between a template QRS complex and the identified QRS complexes to determine an error between the template QRS complex and the identified QRS complexes, wherein the difference function comprises a sum of squared differences between the template QRS complex and the identified QRS complexes,
         applying a logarithm function to the error to determine an expanded error,
         calculating the consistency metric from the expanded error, wherein the consistency metric comprises a Goodness signal, and an amplitude of one or more peaks in the Goodness signal are indicative of a similarity between the template QRS complex and the identified QRS complexes, and
         high pass filtering the Goodness signal to provide a filtered Goodness signal for evaluation of the consistency metric;
   determining a heart rate of the patient;
   determining from the heart rate, the width values and the consistency metric whether a shock criterion is met; and
   discharging, responsive to a determination that a shock criterion is met, at least some of the stored electrical charge through at least one of the plurality of electrodes to deliver a shock to the patient.

17. The non-transitory computer-readable storage medium of claim 16, in which the heart rate is determined based at least in part on the received ECG signal.

18. The non-transitory computer-readable storage medium of claim 16, in which the heart rate is determined based at least in part on a signal received from a heart rate detector.

19. The non-transitory computer-readable storage medium of claim 16, in which the operations further comprise: responsive to the determined heart rate, width values, and consistency metric, classifying the received ECG signal into one of a plurality of rhythm types, the plurality of rhythm types including at least a non-shockable rhythm type, a VF rhythm type, and a VT rhythm type, wherein an ECG signal being classified into the VF rhythm type corresponds to a determination that a shock criterion is met.

20. The non-transitory computer-readable storage medium of claim 19, in which the operations further comprise:
   determining whether one or more delay shock criteria is met based on the heart rate, width values, and consistency metric; and
   in response to a determination that one or more delay shock criteria is met, monitoring the patient's ECG signal for a predetermined time period after the received ECG signal was classified into the VT rhythm type.

21. The non-transitory computer-readable storage medium of claim 20, in which the operations further comprise: responsive to the patient's ECG signal remaining in the VT classification for the predetermined time period, determining that a shock criterion is met.

22. The non-transitory computer-readable storage medium of claim 20, in which the operation of determining whether one or more delay shock criteria is met comprises determining whether an index value, derived from the heart rate and the width values, is greater than a predetermined index threshold or is less than the predetermined index threshold.

23. The non-transitory computer-readable storage medium of claim 22, in which the operation of determining whether one or more delay shock criteria is met further comprises determining whether a consistency metric is greater than a predetermined disorganized threshold or the consistency metric less than the predetermined disorganized threshold.

24. The non-transitory computer-readable storage medium of claim 23, in which responsive to the index value being less than the predetermined index threshold, the operations further comprise determining that one of the one or more delay shock criteria is met.

25. The non-transitory computer-readable storage medium of claim 23, in which responsive to the index value being greater than the predetermined index threshold and the consistency metric is less than the predetermined disorganized threshold, the operations further comprise determining that a shock criterion is met.

* * * * *